United States Patent
Kritzler et al.

(10) Patent No.: US 6,939,836 B2
(45) Date of Patent: Sep. 6, 2005

(54) SURFACTANT SYSTEM

(75) Inventors: Steven Kritzler, Cronulla (AU); Alex Sava, Paddington (AU)

(73) Assignee: Novapharm Research (Australia) Pty Ltd, Rosebery (AU)

(*) Notice: Subject to any disclaimer, the term of this patent is extended or adjusted under 35 U.S.C. 154(b) by 0 days.

(21) Appl. No.: 10/377,294

(22) Filed: Feb. 27, 2003

(65) Prior Publication Data

US 2003/0220222 A1 Nov. 27, 2003

Related U.S. Application Data

(63) Continuation of application No. PCT/AU01/01094, filed on Aug. 30, 2001.

(30) Foreign Application Priority Data

Sep. 1, 2000 (AU) .............................. PQ9844

(51) Int. Cl.[7] .............................. C11D 3/22; C11D 3/28; C11D 3/386
(52) U.S. Cl. ...................... 510/161; 510/179; 510/392; 510/433; 510/470; 510/474; 510/499; 510/500; 134/22.14; 134/25.4; 134/38; 134/39; 134/40; 134/42
(58) Field of Search .................... 510/161, 179, 510/392, 433, 470, 474, 499, 500; 134/22.14, 25.4, 38, 39, 40, 42

(56) References Cited

U.S. PATENT DOCUMENTS

| 5,558,806 A | 9/1996 | Policello et al. |
| 5,846,926 A | 12/1998 | Tracy et al. |
| 5,863,886 A | 1/1999 | Tracy et al. |
| 5,908,619 A | 6/1999 | Scholz |
| 5,922,663 A | 7/1999 | Gabriel et al. |
| 6,040,288 A | 3/2000 | Popoff et al. |
| 2003/0220222 A1 * | 11/2003 | Kritzler et al. ............. 510/470 |

FOREIGN PATENT DOCUMENTS

| EP | WO 99/56793 | * 11/1999 | ............. A61L/2/12 |
| EP | WO 02/018530 | * 3/2002 | ............. C11D/7/32 |

* cited by examiner

*Primary Examiner*—Brian P. Mruk
(74) *Attorney, Agent, or Firm*—Knobbe Martens Olson & Bear LLP

(57) ABSTRACT

The invention relates to an aqueous composition comprising in combination an alkyl pyrrolidone, such as a C8–C18 linear alkyl pyrrolidone, and an alkyl polysaccharide such as an alkyl polyglucoside, and a method of enhancing the efficacy of an enzyme containing composition for use in cleaning medical instruments comprising the step of including in said composition an alkyl pyrrolidone and an alkyl polysaccharide. The methods and compositions of the present invention may further include at least one enzyme such as proteases, lipases, amylases, and cellulases.

29 Claims, 1 Drawing Sheet

SURFACTANT SYSTEM

RELATED APPLICATION

This application is a continuation, under 35 U.S.C. § 120, of International Patent Application No. PCT/AU01/01094, filed on Aug. 30, 2001 under the Patent Cooperation Treaty (PCT), which was published by the International Bureau in English on Mar. 7, 2002, which designates the U.S. and claims the benefit of Australian Provisional Patent Application No. PQ 9844, filed Sep. 1, 2000.

FIELD OF THE INVENTION

The invention relates to a surfactant system for use in aqueous compositions and more particularly to a surfactant system for use in, or addition to, aqueous enzyme based cleaning preparations. The invention has particular advantage when employed in enzyme based cleaning preparations intended for use for cleaning medical instruments.

BACKGROUND OF THE INVENTION

Any discussion of the prior art throughout the specification should in no way be considered as an admission that such prior art is widely known or forms part of common general knowledge in the field.

The invention is herein described with particular reference to compositions for cleaning medical instruments, but is not limited to that use. As herein used the term "medical instruments" is intended broadly to include surgical instruments such as scalpels, biopsy instruments, clamps, and the like; endoscopes, colonoscopes, laparoscopes and other paraphernalia used for surgical investigation or intervention; and other instruments used in the practice of medicine, surgery, and dentistry which require cleaning, disinfection or sterilisation. The term is also intended to include instruments having similar cleaning requirements such as those used in hairdressing, cosmetic treatments, tattooing, body piercing etc as well as other applications where removal of human/animal sebum and/or body secretion is required. Many medical instruments are made from or incorporate a variety of construction materials and cleaning compositions must be such as not to attack any such materials.

It is common practice to clean medical instruments after use with one patient and prior to treatment of another by scrubbing to remove blood, tissue, loose proteinatious and other soils, and then soaking for a predetermined period in an enzyme preparation adapted to further digest or loosen any proteinacious materials remaining on the instrument surface. The instruments are then rinsed clean and subjected to further disinfection or sterilization procedures. To minimize the possibility of cross infection instruments used with one patient are desirably cleaned separately from those used with another.

Preparations for use in cleaning medical instruments consist generally of a concentrate comprising one or more surfactants in combination with one or more proteolytic enzymes. The concentrate is diluted to a working strength (normally a hundredfold dilution) prior to use. One such formulation has been described by NOVO NORDISK ("Novo-formulation"). Three preparations used internationally for this purpose are EPIZYME® (a product of 3M), MEDIZYME® (a product of Whiteley Industries Pty Ltd., Sydney Australia) and ENDOZYME® (a product of Ruholf Corporation, N.Y., USA). While such products are generally effective and widely used there remains a need for products which are more efficient, and especially for preparations which are capable of achieving a predetermined level of effectiveness within a shorter time than those currently available.

The concentrate must be sufficiently stable in transit and storage prior to use to satisfy the needs of commerce. The choice of surfactants which in practice can be formulated in concentrated aqueous solutions is limited. Either the surfactants limit the storage stability of the concentrate, resulting in problems of foaming on dilution, provide insufficient reduction in surface tension, destabilize other components of the system such as enzymes, or suffer from other disadvantages. Mostly, formulators utilize surfactants chosen from a small group of conventional and well known nonionic surfactants which have been found to be satisfactory for such uses, but there remains an unsatisfied demand for formulations of improved efficiency.

It is an object of the invention to provide an improved surfactant system, and of preferred embodiments of the invention to provide an enzyme based cleaning composition which avoids problems of the prior art and/or provides improved performance.

SUMMARY OF THE INVENTION

According to a first aspect the invention provides an aqueous composition comprising in combination an alkyl pyrrolidone and an alkyl polysaccharide.

For preference the alkyl pyrrolidone is a C8–C18 linear alkyl pyrrolidone. N-dodecyl pyrrolidone ("N-DP") is highly preferred. Desirably, the alkyl polysaccharide is an alkyl polyglucoside ("APG").

According to a second aspect the invention provides a method of enhancing the efficacy of an enzyme containing composition for use in cleaning medical instruments comprising the step of including an alkyl pyrrolidone and an alkyl polysaccharide.

Preferably the composition is a concentrate which contains surfactant according to the first aspect as part of its formulation, but the surfactant system can be added subsequently either to the concentrate or the working solution.

According to a third aspect the invention provides a method of cleaning a medical instrument including the step of treating the instrument with a composition including at least one enzyme, an alkyl pyrrolidone and an alkyl polysaccharide.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Alkylpyrrolidones are known to reduce surface tension progressively with increasing concentration in water achieving a minimum surface tension (maximum effectiveness) at a concentration of about 0.1% in the case of dodecyl pyrrolidone and about 0.002% in the case of octyl pyrrolidone, which concentrations correspond to the maximum solubility of the respective pyrrolidones in water. This has in the past inhibited their use in concentrates, since the maximum concentration in an aqueous system is inevitably less than fully effective as a surfactant when diluted to any substantial degree.

DETAILED DESCRIPTION OF THE PREFERRED EMBODIMENT

Figure 1:
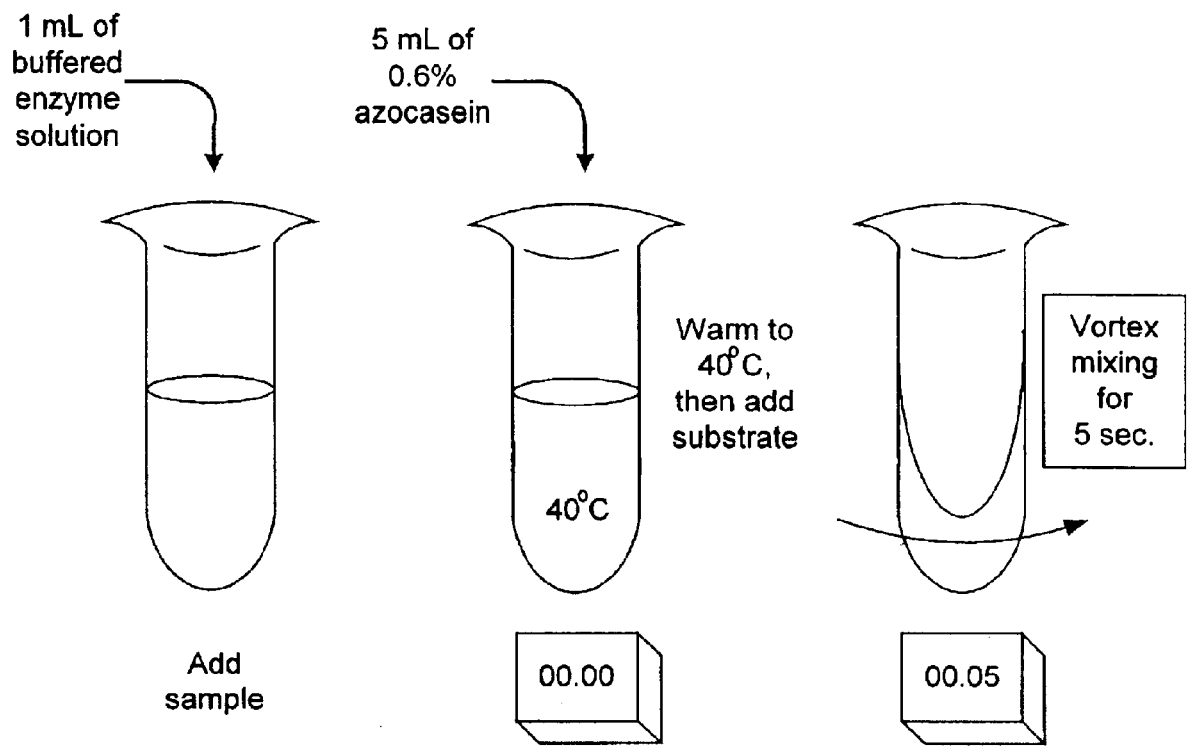
FIG. 1 provides a diagrammatic representation of a manual procedure for determination of proteolytic activity in enzyme preparations and detergents (azocasein substrate).
Figure 1:
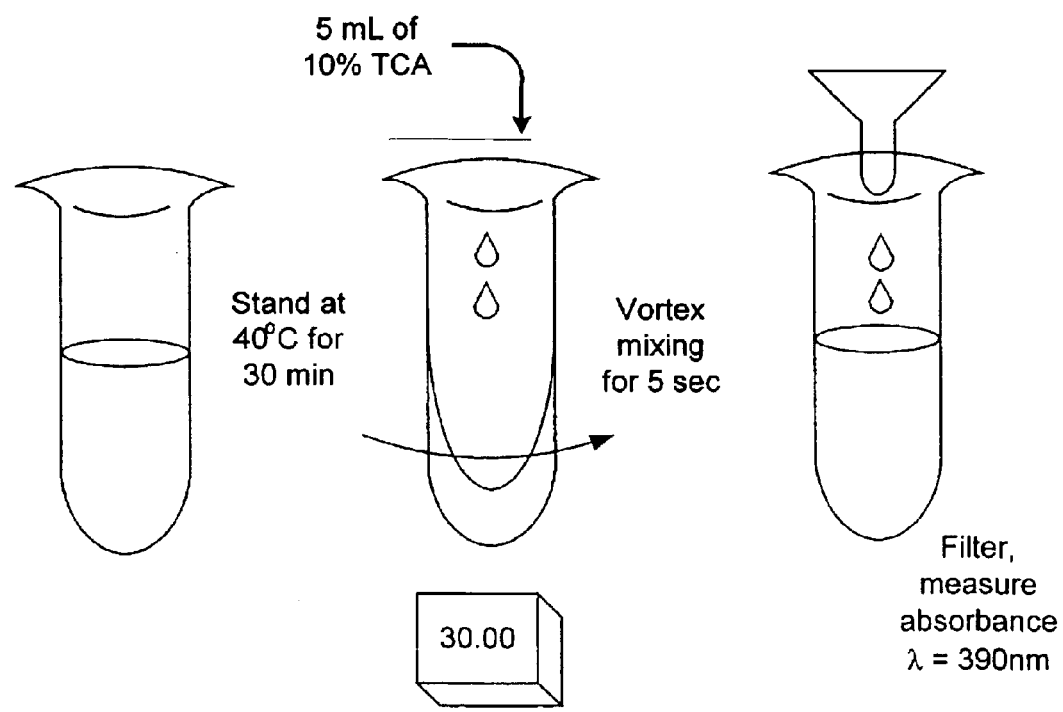

An additive according to the invention consisting of n-dodecyl pyrrolidone ("n-DP") in combination with alkyl polyglucoside ("APG") was added to solutions prepared from each of three commercially available enzyme cleaning preparation concentrates. These were MEDIZYME®, ENDOZYME® and EPIZYME®. A fourth concentrate "NOVO formulation", a product described by NOVO INDUSTRIES in Novo Nordisk Publications Application Sheet B-613, "Application of Enzymes in Detergents for Endoscope Cleaning", was also prepared and tested. In the tests described in Table 1 the additive consisted of 0.2% w/w n-dodecyl pyrrolidone ("n-DP") and 0.1% w/w of alkyl polyglucoside ("APG") in each case based on the weight of the concentrate.

The NOVO Formulation (Concentrate) is as follows:

| Component | % w/w |
| --- | --- |
| Non-ionic surfactant (Teric BL9) | 12 |
| Propylene Glycol | 22 |
| Triethanolamine | 7 |
| Boric acid | 4 |
| Calcium Chloride | 0.1 |
| Savinase 16.0 L (Protease) | 13 |
| Termamyl (Amylase) | 7 |
| Water | to 100 |
| pH | 7 |

The Epizyme composition (Concentrate) is as follows:

| Component | % w/w |
| --- | --- |
| Tap water | 19.0 |
| Teric BL9 (non ionic surfactant) | 10.0 |
| Preservative | 0.15 |
| Enzyme stabilizer | 6.0 |
| 50% caustic soda | 2.5 |
| Propylene Glycol | 6.0 |
| Protease | 10.0 |
| Lipase | 0.2 |
| Amylase | 1.5 |
| Cellulase | 0.5 |
| Perfume | 0.15 |
| Water | to 100.0 |

By way of example the protease may be subtilisin, the amylase Alpha-amylase, the cellulase may be endo-1,4-beta-glucanase and the lipase may be Triacylglycerol. However, other enzymes or combinations of enzymes may be substituted for these.

Each of the cleaning composition concentrates were diluted at a rate of 1 part of concentrate in 100 parts of standard hard water (0.304 g calcium chloride and 0.065 g of magnesium chloride per 1 L of distilled water. Therapeutic Goods Order 54 & Guidelines, 1996, p. 17). The efficacy of each product was then tested against standard soil preparations on glass slides, (1) neat and (2) with the addition of an additive according to the invention. The efficiency of the preparation (time required to achieve a given score) was measured at various temperatures. The results are shown in Table 1 in comparison with results of compositions including the additive according to the invention.

Accelerated aging tests are summarized in Table 2. Details of the preparation of standard soils is given in table 3 and "*Methods for Ascertaining the Cleaning Performance of Dishwasher Detergents*" (SOFW-Journal, 126. Jahrgang 3-2000)

TABLE 1

Soil carrier glass microscope slides

| | NOVO-formulation | | | | | | | |
| --- | --- | --- | --- | --- | --- | --- | --- | --- |
| | With | EPIZYME | | MEDIZYME | | ENDOZYME | | |
| | APG + | | With APG + | | With APG + | | With APG + | |
| | neat | n-DP | neat | n-DP | neat | n-DP | neat | n-DP |
| Burnt minced meat. Contact time (min) required to achieve score 8. | | | | | | | | |
| 25° C. | 95 | 68 | 67 | 47 | 120 | 93 | >480 | 241 |
| 40° C. | 60 | 46 | 52 | 37 | 87 | 71 | 212 | 157 |
| 50° C. | 42 | 33 | 30 | 19 | 65 | 53 | 170 | 140 |
| Milk in microwave. Contact time (in min) required to achieve score 10 (full removal) | | | | | | | | |
| 25° C. | 53 | 38 | 35 | 25 | 39 | 30 | 69 | 51 |
| 40° C. | 39 | 31 | 24 | 19 | 29 | 23 | 50 | 35 |
| 50° C. | 27 | 22 | 12 | 10 | 19 | 16 | 31 | 28 |
| Edinburgh Soil. Contact time (in min) required to achieve score 10 (full removal) | | | | | | | | |
| 25° C. | 28 | 25 | 21 | 19 | 26 | 23 | 32 | 28 |
| 40° C. | 21 | 20 | 11 | 10 | 17 | 11.5 | 25 | 35 |
| 50° C. | 18 | 15 | 9 | 9 | 11 | 10 | 18 | 16 |

N-DP: N-dodecyl pyrrolidone (Surfadone LP 300 from International Speciality Products), APG: Alkyl polyglucoside (ALKADET 15 from Huntsman Corporation Australia)

Addition rate: 0.2 w/w % N-DP and 0.1 w/w % APG to concentrate

Dilution rate: 1 part of concentrate in 100 parts of standard hard water

As is evident from Table 1, the addition of the additive reduces the time required for the composition to achieve a given score and does so at each temperature. The additive is especially effective at lower temperatures.

Although the results shown in Table 1 were obtained using 0.2 w/w % N-DP and 0.1 w/w % APG to concentrate, the ratio of N-DP to APG can be varied. It is preferred that the ratio be between 1 part by weight of alkyl pyrrolidone to 3 parts by weight of alkyl polyglucoside and 3 parts by weight of alkyl pyrrolidone to 1 part by weight of alkyl polyglucoside, more preferably between 3 parts by weight of alkyl pyrrolidone to 1 parts by weight of alkyl polyglucoside and 1 part by weight of alkyl pyrrolidone to 1 part by weight of alkyl polyglucoside.

The concentration of N-DP and APG is each preferably less than 7.5% w/w of the concentrate (ie less than about 0.0075% in the concentrate at dilution of 1 part concentrate:100 parts water) and more preferably is less than 3% w/w. The actual concentrations employed will depend on the surface tension properties required, the hydrophilicity of the alkyl polyglucosides and the degree of hydrotroping provided by other excipients in the formulation to the alkyl polyglucoside, as well as other factors which may occur with respect to individual formulations.

Table 2 shows the effect of the additive in accelerated aging tests. The results demonstrate that the additive slightly improves storage stability, or, at least, does not adversely affect it.

TABLE 2

Remaining Protease Activity in % for concentrated formulations after 21 days storage (100% at day 0):

| | NOVO-formulation | | EPIZYME | | MEDIZYME | | ENDOZYME | |
|---|---|---|---|---|---|---|---|---|
| | Neat | With APG + n-DP | neat | With APG + n-DP | neat | With APG + n-DP | neat | With APG + n-DP |
| 25° C. | 95 | 95 | 96 | 98 | 95 | 95 | 93 | 93 |
| 40° C. | 89 | 89 | 91 | 91 | 85 | 85 | 80 | 83 |
| 47° C. | 77 | 84 | 85 | 87 | 69 | 74 | 73 | 78 |

Assessed using B 863b test method by NOVO NORDISK (attached herewith as Annexure 1). The additive according to the invention and dilution were as for table 1.

Table 3 shows the effects of varying the concentration and ratio of the alkylpyrrolidone and alkylpolyglucoside. It can be seen that the composition is efficacious in reducing contact times for cleaning over a wide range of alkylpyrroline to alkylpolyglucoside ratios.

TABLE 3

Soil carrier: glass microscope slides

| | NOVO-formulation | | Epizyme | |
|---|---|---|---|---|
| | neat | With APG + SURF | Neat | With APG + SURF |
| Burnt minced meat. Contact time (min) required to achieve score 8. | | | | |
| 25° C. | 95 | 66 | 67 | 48 |
| 40° C. | 60 | 49 | 52 | 39 |
| 50° C. | 42 | 32 | 30 | 22 |
| Milk in microwave. Contact time (in min) required to achieve score 10 (full removal) | | | | |
| 25° C. | 53 | 34 | 35 | 21 |
| 40° C. | 39 | 29 | 24 | 17 |
| 50° C. | 27 | 20 | 12 | 8 |
| Edinburgh Soil. Contact time (in min) required to achieve score 10 (full removal) | | | | |
| 25° C. | 28 | 22 | 21 | 19 |
| 40° C. | 21 | 16 | 11 | 9 |
| 50° C. | 18 | 19 | 9 | 8 |

SURF: n-dodecyl pyrrolidone (Surfadone LP 300 from International Speciality Products),
APG: Alkyl polyglucoside (ALKADET 15 from Huntsman Corporation Australia)
Addition rate: 0.2 w/w % SURF and 1% APG to concentrate
Dilution rate: 1 part of concentrate in 100 parts of standard hard water Results.

| | NOVO-formulation | | Epizyme | |
|---|---|---|---|---|
| | neat | With APG + SURF | neat | With APG + SURF |
| Burnt minced meat. Contact time (min) required to achieve score 8. | | | | |
| 25° C. | 95 | 64 | 67 | 44 |
| 40° C. | 60 | 47 | 52 | 37 |
| 50° C. | 42 | 31 | 30 | 22 |
| Milk in microwave. Contact time (in min) required to achieve score 10 (full removal) | | | | |
| 25° C. | 53 | 34 | 35 | 21 |
| 40° C. | 39 | 28 | 24 | 16 |
| 50° C. | 27 | 20 | 12 | 7 |
| Edinburgh Soil. Contact time (in min) required to achieve score 10 (full removal) | | | | |
| 25° C. | 28 | 21 | 21 | 19 |
| 40° C. | 21 | 15 | 11 | 9 |
| 50° C. | 18 | 14 | 9 | 7 |

SURF: n-dodecyl pyrrolidone (Surfadone LP 300 from International Speciality Products),
APG: Alkyl polyglucoside (ALKADET 15 from Huntsman Corporation Australia)
Addition rate: 0.2 w/w % SURF and 7.5% APG to concentrate
Dilution rate: 1 part of concentrate in 100 parts of standard hard water Results.

Soil carrier: glass microscope slides

| | NOVO-formulation | | Epizyme | |
|---|---|---|---|---|
| | neat | With APG + SURF | neat | With APG + SURF |
| Burnt minced meat. Contact time (min) required to achieve score 8. | | | | |
| 25° C. | 95 | 67 | 67 | 44 |
| 40° C. | 60 | 44 | 52 | 41 |
| 50° C. | 42 | 30 | 30 | 20 |
| Milk in microwave. Contact time (in min) required to achieve score 10 (full removal) | | | | |
| 25° C. | 53 | 37 | 35 | 24 |
| 40° C. | 39 | 26 | 24 | 15 |
| 50° C. | 27 | 18 | 12 | 12 |
| Edinburgh Soil. Contact time (in min) required to achieve score 10 (full removal) | | | | |
| 25° C. | 28 | 18 | 21 | 19 |
| 40° C. | 21 | 15 | 11 | 12 |
| 50° C. | 18 | 12 | 9 | 7 |

SURF: n-dodecyl pyrrolidone (Surfadone LP 300 from International Speciality Products),
APG: Alkyl polyglucoside (ALKADET 15 from Huntsman Corporation Australia)
Addition rate: 1% w/w % SURF and 0.1% APG to concentrate
Dilution rate: 1 part of concentrate in 100 parts of standard hard water Results.

| Soil carrier: glass microscope slides | | | | |
|---|---|---|---|---|
| | NOVO-formulation | | Epizyme | |
| | neat | With APG + SURF | neat | With APG + SURF |
| Burnt minced meat. Contact time (min) required to achieve score 8. | | | | |
| 25° C. | 95 | 63 | 67 | 49 |
| 40° C. | 60 | 52 | 52 | 37 |
| 50° C. | 42 | 35 | 30 | 23 |
| Milk in microwave. Contact time (in min) required to achieve score 10 (full removal) | | | | |
| 25° C. | 53 | 35 | 35 | 24 |
| 40° C. | 39 | 27 | 24 | 16 |
| 50° C. | 27 | 24 | 12 | 9 |
| Edinburgh Soil. Contact time (in min) required to achieve score 10 (full removal) | | | | |
| 25° C. | 28 | 23 | 21 | 20 |
| 40° C. | 21 | 17 | 11 | 9 |
| 50° C. | 18 | 12 | 9 | 7 |

SURF: n-dodecyl pyrrolidone (Surfadone LP 300 from International Speciality Products),
APG: Alkyl polyglucoside (ALKADET 15 from Huntsman Corporation Australia)
Addition rate: 7.5% w/w % SURF and 0.1% APG to concentrate
Dilution rate: 1 part of concentrate in 100 parts of standard hard water
Assessed using B 863B test method by NOVO NORDISK (attached)

TABLE 4

SOIL COMPOSITION & DETERGENT ENZYME ACTIVITY TEST

Milk in Microwave:

- 60 ml of milk
- 6 beakers
- a microwave set to 450 W
- an oven heater set to 80 C.°

The microwave was pre-heated by placing 6 water-filled beakers in a circle on the glass turn-table and leaving it on "high" (900 W) for 10 minutes. Then, the beakers with water were replaced by beakers with 10 ml of milk. The milk was heated for 10 minutes at 450 W, then allowed to cool, forming a skin, and placed into an oven for 2 hours at 80° C.

Mince meat:

- 20 grams of beef mince
- 7.5 grams of egg yolk and whites
- 8.0 gram of water
- 30 × 30 mm polar substrate (ceramic tiles)

The mince was mixed with the egg yolk and water with the use of a hand blender. 1 g of homogenized mixture was spooned onto 3 × 3 cm ceramic tiles, onto the smooth side.
Then the tiles were left in an oven for 10 minutes.

Edinburgh Soil

- 20 g egg yolk
- 20 g water
- 0.5 g cholesterol
- 3 g beef gelatin
- 0.45 hog mucin The beef gelatin and water were blended together and heated until the mixture obtained a homogenous consistency. Cholesterol, hog mucin and egg yolk were blended in after gelatin was cooled to 30C. 0.1 g of soil was deposited onto surfaces of the microscope slides. The smears were made of a uniform thickness for each set of slides; the thickness was regulated by a border of adhesive tape along each border of the smearing instrument In order to simulate the conditions of an endoscope cleaning, the slides were left to dry in open air at 20° C. for 20 minutes.

Without wishing to be bound by theory, the polysaccharide appears to stabilize the pyrrolidone, the combination being more soluble in the concentrate and resulting in substantially improved lowering of surface tension at the working dilution.

Although the test results utilize n-dodecyl pyrrolidone, other alkyl pyrrolidones could be substituted therefore, and especially C8 to C18 alkyl pyrrolidones. The amount to be added can be determined by simple trial but in general increasing the concentration significantly above the levels herein employed tends to give a decreasing advantage. Similarly, other alkyl polysaccharides may be substituted for APG. For example other sugar units and derivatives of sugar units may be substituted for glucose units. Again there is an optimum concentration beyond which increasing the concentration is of relatively little benefit. While the combination of n-alkyl pyrrolidone with APG is highly preferred, beneficial effects are obtainable with at least some soils by adding it in isolation. The optimum ratio of n-DP to APG can be determined by simple trial for a given concentrate.

The combination of the invention provides an improved surfactant system which is expected to have application in many end-uses. In the field of cleaners for medical instruments, the surfactant system of the invention may be simply added to commercially available enzyme cleaning products either to the concentrate or, at an appropriate dilution to the working solution prior to use. Preferably however the additives are incorporated into a concentrate at the time of manufacture of the concentrate which is then merely diluted prior to use.

Additives according to the invention may be added to dishwashing, hand washing and other surface cleaning compositions.

Embodiments of the invention may be altered and may have other chemicals added or substituted therefore to an extent which will be apparent to those skilled in the art from the teaching hereof without departing from the inventive concept herein disclosed.

EXAMPLE

Novo Nordisk B 863b-GB

Manual Procedure for Determination of Proteolytic Activity in Enzyme Preparations and Detergents (Azocasein Substrate)

A diagrammatic representation of this method is shown in FIG. 1.

Principle

A protease is allowed to hydrolyse azocasein for 30 minutes at 40° C. Undigested protein is precipitated with trichloroacetic acid and the quantity of digested product is determined by spectrophotometry.

Enzyme Unit Definition

No separate unit is defined. Activity is determined relative to a standard of known activity and the result given in the same units as used for the standard.

Assay Conditions

| | |
|---|---|
| pH: | 8.5 (0.2 M Tris-SO$_4$ buffer) |
| Temperature: | 40° C. |
| Substrate: | 0.5% azocasein (in reaction mixture) |
| Reaction time: | 30 minutes |

Apparatus
Spectrophotometer to read absorbance at 390 nm
pH meter
Water bath at 40° C.·0.5° C.
Timer with a second hand
Vortex mixer
16·125 mm test tubes
Repeating dispenser, 5 ml capacity
Small funnels and filter paper, Whatman no. 3 or equivalent
Reagents
1. 2.0 M Tris buffer stock solution
Dissolve 242 g trishydroxymethylaminomethane (Sigma "Trizma Base" T-1503 or equivalent) in 700–800 ml deionised water.
Adjust pH to 8.5 with 10 N $H_2SO_4$.
Adjust volume to 1 litre.
This concentrate is to be used at 10 ml/100 ml volume for all final dilutions with 0.2 M Tris buffer.
2. 50% urea solution
Dissolve 50 g urea (analytical grade) in 50 ml warm deionised water.
Adjust volume to 1 litre.
3. 10% trichloroacetic acid solution (stop reagent)
Dissolve 100 g trichloroacetic add (TCA) in 200 ml deionised water.
Adjust volume to 1 litre.
4. Azoecasein (substrate solution)
Make fresh daily-discard any unused substrate
In a 250-ml beaker:
Weigh 0.6 g azocasein (Sigma A-2765).
Add 10 ml 50% urea solution and mix until dissolved.
  Add 10 ml 2.0 M Tris buffer stock solution.
  Add 30–50 ml deionised water and continue stirring until clear of particles.
  Adjust pH to 8.5 using dilute $H_2SO_4$. Adjust volume to 100 ml and mix thoroughly. Keep cool until ready to begin assay.
5. Enzyme samples and standards
See Appendix I for Alcalase®, Appendix II for Esperase® and Savinase®, and Appendix III for Durazym®.
  After dissolving a detergent sample for protease assay, it is strongly recommended that the pH of this solution be checked and, if needed, adjusted to 8.5·0.1 units.
  If it is desired to know the exact activity levels of proteinase in a detergent, the detergent bases should be included in the standard solutions unless it is already known that the particular formulation being used has no effect on the protease activity. The concentration of the base detergent should be equal to that used in the sample solution of the detergent containing protease.
  The presence in solution of strong chelators such as NTA or EDTA may result in deactivation of the protease over the time period required for preparation of the various materials for the assay. This cause of deactivation can be overcome by adding excess calcium to the sample solutions.
Procedure
1. Preheat water bath to 40° C.±0.5° C. (approx. 1 hr.).
2. Approx. 10 minutes before starting assay, place substrate solution in 40° C. water bath to equilibrate.
3. To appropriately labelled test tubes, pipet 1 ml of sample or enzyme standard and equilibrate to 40° C. in water bath (approx. 1 minute).
4. Start reaction:
  At precisely timed intervals, add 5 ml substrate solution to each tube containing sample or standard, vortex and return to water bath for 30 minutes.
  Sample blank:
  To sample blank add 5 ml 10% TCA and vortex; then add 5 ml substrate solution, vortex and let stand at room temperature until ready to filter.
5. Stop reaction:
  After exactly 30 minutes, at the same time intervals as before, add 5 ml of 10% TCA to each sample or standard tube, vortex and let stand at room temperature
6. After 15–20 minutes filter all tubes by gravity filtration through paper filters into clean, dry and properly-labelled test tubes.
7. Read absorbances at 390 nm vs deionised water blank.
Calculations
1. Standard curve:
  a) If standard blank ($A_0$, $E_0$ or $S_0$,)>0.16, assay should be re-run with fresh substrate
  b) If standard blank <0.16, subtract its $A_{390}$ readings from standards to obtain •absorbance
  c) Plot a curve of •absorbance vs proteolytic activity (AU or KNPU/tube=AU or KNPU/ml of final dilution).
2. Sample tubes:
  •absorbance=$A_{sample}-A_{blank}$
  Using standard curve, determine activity of sample/tube, $$\text{Activity/gram} = \frac{(\text{activity/tube}) \cdot (\text{dilution factor})}{\text{gram of sample}}$$

Alcalase®
Unit definition: Anson Unit (AU)
1 Anson Unit=the amount of enzyme* which digests haemoglobin A an initial rate such that there is liberated per minute an amount of TCA-soluble product which gives the same colour with phenol reagent as one milliequivalent of tyrosine.

* Under reaction conditions given in the NNAS method AF4/5-GB: Modified Anson—Haemoglobin Method for the Determination of Proteolytic Activity.

A standard curve is prepared using an enzyme whose activity in Anson Units is known. Unknowns are then compared to this curve.
Buffer: 0.2 M Tris, pH 8.5
Sample activity range: $5 \cdot 10^{-5}$–$15 \cdot 10^{-5}$ AU/ml
Standard blank: 1 ml of 0.2 M Tris buffer pH 8.5=$A_0$
Substrate: Azocasein solution, 0.5%, pH 8.5
Sample Preparation:
Dissolve an accurately-weighed amount of sample in an accurately-known volume of 0.2 M Tris buffer so that the solution contains between $5 \cdot 10^{-5}$ and $15 \cdot 10^{-5}$ AU/ml and has a pH of 8.5.
N.B. For each unknown, prepare a sample blank and one or more duplicates (as necessary).
Keep solutions on ice until ready to assay.
Standard Curve
Enzyme standard stock solution: Dissolve accurately-weighed Alcalase standard in 100 ml 0.2 M Tris buffer (pH 8.5) to yield $2.6 \cdot 10^{-3}$ AU/ml
Dilute the stock solution as follows:

| Tube 1 label | Stock solution | 2 M Tris buffer stock | Final volume | Activity |
|---|---|---|---|---|
| $A_0$ | 0 ml | 10 ml | 100 ml | $0.0 \cdot 10^{-5}$ AU/ml |
| $A_1$ | 1 ml | 10 ml | 100 ml | $2.6 \cdot 10^{-5}$ AU/ml |
| $A_2$ | 2 ml | 10 ml | 100 ml | $5.2 \cdot 10^{-5}$ AU/ml |
| $A_3$ | 3 ml | 10 ml | 100 ml | $7.8 \cdot 10^{-5}$ AU/ml |

-continued

| Tube 1 label | Stock solution | 2 M Tris buffer stock | Final volume | Activity |
|---|---|---|---|---|
| $A_4$ | 4 ml | 10 ml | 100 ml | $10.4 \cdot 10^{-5}$ AU/ml |
| $A_5$ | 5 ml | 10 ml | 100 ml | $13.0 \cdot 10^{-5}$ AU/ml |
| $A_6$ | 6 ml | 10 ml | 100 ml | $15.6 \cdot 10^{-5}$ AU/ml |

Savinase®/Esperase®
Unit definition: Kilo Novo Protease Unit (KNPU)
1 KNPU=1000 NIPU
1 Novo Protease Unit (NPU)=the amount of enzyme* which hydrolyzes casein at such a rate that the initial rate of formation of peptides/minute corresponds to 1 micromole of glycine/minute
* Standard conditions given in NNAS method 162/3-GB: Manual DMC Method for the Determination of Proteolytic Activity.
A standard curve is prepared using an enzyme whose activity in KNPU is known. Unknowns are then compared to this curve
Buffer: 0.2 M Tris, pH 8.5
Sample activity range: $2 \cdot 10^{-4} - 6 \cdot 10^{-4}$ KNPU/ml
Standard blank: 1 ml of 0.2 M Tris buffer pH 8.5=$E_0$ or $S_0$
Substrate: Azocasein solution, 0.5%, pH 8.5
Sample Preparation:
Dissolve an accurately-weighed amount of sample in an accurately-known volume of 0.2 M Tris buffer so that the solution contains between $2 \cdot 10^{-4} - 6 \cdot 10^{-4}$ KNPU/ml and has a pH of 8.5.
N. B. For each unknown, prepare a sample blank and one or more duplicates (as necessary). Keep solutions on ice until ready to assay.
Standard Curve
Enzyme standard stock solution: Dissolve accurately-weighed Savinase or Esperase standard in 100 mil 0.2 M Tris buffer (pH 8.5) to yield $1 \cdot 10^{-2}$ KNPU/ml.
Dilute the stock solution as follows:

| Tube | Stock solution | 2 M Tris buffer stock | Final volume | Activity |
|---|---|---|---|---|
| $E_0$ or $S_0$ | 0 ml | 10 ml | 100 ml | $0.0 \cdot 10^{-4}$ KNPU/ml |
| $E_1$ or $S_1$ | 1 ml | 10 ml | 100 ml | $1.0 \cdot 10^{-4}$ KNPU/ml |
| $E_2$ or $S_2$ | 2 ml | 10 ml | 100 ml | $2.0 \cdot 10^{-4}$ KNPU/ml |
| $E_3$ or $S_3$ | 3 ml | 10 ml | 100 ml | $3.0 \cdot 10^{-4}$ KNPU/ml |
| $E_4$ or $S_4$ | 4 ml | 10 ml | 100 ml | $4.0 \cdot 10^{-4}$ KNPU/ml |
| $E_5$ or $S_5$ | 5 ml | 10 ml | 100 ml | $5.0 \cdot 10^{-4}$ KNPU/ml |
| $E_6$ or $S_6$ | 6 ml | 10 ml | 100 ml | $6.0 \cdot 10^{-4}$ KNPU/ml |

E = Esperase, S = Savinase

Durazym®
Unit definition: Durazym Protease Unit (DPU)
The activity is measured relative to a Durazym standard with the same units as the sample i.e. DPU.
A standard curve is prepared using an enzyme whose activity in DPU is known. Unknowns we then compared to this curve
Buffer: 0.2 M Tris, pH 8.5
  Sample activity range: $6 \cdot 10^{-4} - 18 \cdot 10^{-4}$ DPU/ml
  Standard blank: 1 ml of 0.2 M Tris buffer pH 8.5=$D_0$
  Substrate: Azocasein solution, 0.5%, pH 8.5
Sample Preparation:
Dissolve an accurately-weighed amount of sample in an accurately-known volume of 0.2 M Tris buffer so that the solution contains between $6 \cdot 10^{-4} - 18 \cdot 10^{-4}$ DPU/ml and has a pH of 8.5.
N.B. For each unknown, prepare a sample blank and one or more duplicates (as necessary). Keep solutions on ice until ready to assay.
Standard Curve
Enzyme standard stock solution: Dissolve accurately-weighed Durazym standard in 100 ml 0.2 M Tris buffer (pH 8.5) to yield $1 \cdot 10^{-2}$ DPU/ml
Dilute the stock solution as follows:

| Tube label | Stock solution | 2 M Tris buffer stock | Final volume | Activity |
|---|---|---|---|---|
| $D_0$ | 0 ml | 10 ml | 100 ml | $0.0 \cdot 10^{-4}$ DPU/ml |
| $D_1$ | 3 ml | 10 ml | 100 ml | $3.0 \cdot 10^{-4}$ DPU/ml |
| $D_2$ | 6 ml | 10 ml | 100 ml | $6.0 \cdot 10^{-4}$ DPU/ml |
| $D_3$ | 9 ml | 10 ml | 100 ml | $9.0 \cdot 10^{-4}$ DPU/ml |
| $D_4$ | 12 ml | 10 ml | 100 ml | $12.0 \cdot 10^{-4}$ DPU/ml |
| $D_5$ | 15 ml | 10 ml | 100 ml | $15.0 \cdot 10^{-4}$ DPU/ml |
| $D_6$ | 18 ml | 10 ml | 100 ml | $18.0 \cdot 10^{-4}$ DPU/ml |

What is claimed is:

1. An aqueous composition for enhancing the efficacy of an enzyme containing cleaning solution for use in cleaning medical instruments, comprising in combination an alkyl pyrrolidone and an alkyl polysaccharide, wherein the efficacy of said cleaning solution is enhanced for use at a temperature of 25–50° C., wherein the alkyl pyrrolidone is a C8–C18 linear alkyl pyrrolidone.

2. A composition according to claim 1 wherein the alkyl pyrrolidone is n-dodecyl pyrrolidone.

3. A composition according to claim 1 wherein the alkyl polysaccharide is an alkyl polyglucoside.

4. A composition according to claim 1 wherein the ratio of alkyl pyrrolidone to alkyl polysaccharide is between a ratio of 1 part by weight of alkyl pyrrolidone to 3 parts by weight of alkyl polysaccharide and 3 parts by weight of alkyl pyrrolidone to 1 part by weight of alkyl polysaccharide.

5. A composition according to claim 4 wherein the ratio of alkyl pyrrolidone to alkyl polysaccharide is between a ratio of 1 part by weight of alkyl pyrrolidone to 3 parts by weight of alkyl polysaccharide and 1 parts by weight of alkyl pyrrolidone to 1 part by weight of alkyl polysaccharide.

6. A composition according to claim 5 comprising about 1 part by weight of alkyl pyrrolidone to about 1 part by weight of alkyl polysaccharide.

7. A composition according to claim 1 further including at least one enzyme.

8. A composition according to claim 7 including at least one enzyme selected from the group consisting of proteases, lipases, amylases, and cellulases.

9. A composition according to claim 8 including at least two different enzymes each selected from the group consisting of proteases, lipases, amylases, and cellulases.

10. A composition according to claim 7 further comprising propylene glycol.

11. A composition according to claim 7 further comprising a non ionic surfactant.

12. A composition according to claim 7 wherein alkyl polysaccharide is present in a concentration of less than 7.5% w/w.

13. A composition according to claim 12 wherein alkyl polysaccharide is present in a concentration of less than 0.3% w/w.

14. A composition according to claim 7 wherein alkyl pyrrolidone is present in a concentration of less than 7.5% w/w.

15. A composition according to claim 14 wherein alkyl pyrrolidone is present in a concentration of less than 0.3% w/w.

16. A method of enhancing the efficacy of an enzyme containing composition for use in cleaning medical instruments comprising the step of including in said composition an alkyl pyrrolidone and an alkyl polysaccharide wherein said cleaning composition is used at a temperature of 25–50° C.

17. A method according to claim 16 wherein in combination an alkyl pyrrolidone and an alkyl polysaccharide is added to an enzyme containing composition.

18. A method according to claim 16 wherein an alkyl pyrrolidone and an alkyl polysaccharide are separately added to an enzyme containing composition.

19. A method according to claim 17 wherein the enzyme containing composition is a concentrate and the alkyl pyrrolidone and an alkyl polysaccharide are added to the concentrate prior to its dilution to a working strength.

20. A method according to claim 16 wherein an alkyl pyrrolidone and an alkyl polysaccharide are each formulated in combination with one or more enzymes to produce a concentrate suitable for dilution to provide an enzyme cleaning solution.

21. The method of claim 16 wherein the alkyl polysaccharide is alkyl polyglucoside.

22. The method of claim 16 wherein the alkyl pyrrolidone is n-dodecyl pyrrolidone.

23. A method of cleaning a medical instrument including the step of treating the instrument with a composition including at least one enzyme, an alkyl pyrrolidone and an alkyl polysaccharide at a temperature of 25–50° C.

24. A method according to claim 23 wherein the alkyl pyrrolidone is a C8–C18 linear alkyl pyrrolidone.

25. A method according to claim 24 wherein the alkyl pyrrolidone is n-dodecyl pyrrolidone.

26. A method according to claim 23 wherein the alkyl polysaccharide is an alkyl polyglucoside.

27. A method according to claim 23 wherein the ratio of alkyl pyrrolidone to alkyl polysaccharide is between a ratio of 1 part by weight of alkyl pyrrolidone to 3 parts by weight of alkyl polysaccharide and 3 parts by weight of alkyl pyrrolidone to 1 part by weight of alkyl polysaccharide.

28. A method according to claim 27 wherein the ratio of alkyl pyrrolidone to alkyl polysaccharide is between a ratio of 1 part by weight of alkyl pyrrolidone to 3 parts by weight of alkyl polysaccharide and 1 parts by weight of alkyl pyrrolidone to 1 part by weight of alkyl polysaccharide.

29. A method according to claim 23 comprising about 1 part by weight of alkyl pyrrolidone to about 1 part by weight of alkyl polysaccharide.

* * * * *